(12) United States Patent
Christensen (10) Patent No.: US 7,758,345 B1
(45) Date of Patent: Jul. 20, 2010

(54) SYSTEMS AND METHODS FOR DESIGN AND MANUFACTURE OF A MODIFIED BONE MODEL INCLUDING AN ACCURATE SOFT TISSUE MODEL

(75) Inventor: Andrew M Christensen, Littleton, CO (US)

(73) Assignee: Medical Modeling Inc., Golden, CO (US)

( * ) Notice: Subject to any disclaimer, the term of this patent is extended or adjusted under 35 U.S.C. 154(b) by 610 days.

(21) Appl. No.: 11/694,595

(22) Filed: Mar. 30, 2007

Related U.S. Application Data

(60) Provisional application No. 60/787,747, filed on Apr. 1, 2006.

(51) Int. Cl.
*A61C 9/00* (2006.01)
(52) U.S. Cl. ....................................... 433/214; 433/213

(58) Field of Classification Search ................. 433/213, 433/214, 167, 168.1, 171; 264/16, 17
See application file for complete search history.

(56) References Cited

U.S. PATENT DOCUMENTS

5,320,529 A    6/1994    Pompa

*Primary Examiner*—Ralph A Lewis
*Assistant Examiner*—Eric Rosen
(74) *Attorney, Agent, or Firm*—Faegre & Benson LLP (57) ABSTRACT

Systems and methods for creation of anatomically correct physical models for an individual patient are provided. More specifically, the embodiments of the present invention relate to systems and methods for design and manufacture of a modified bone model including an accurate soft tissue model. Medical image acquisition processes are used to capture data representative of an anatomy and a scan prosthesis. A modified bone model with supports is designed and fabricated. The modified bone model and scan prosthesis (or copy thereof) is then used to generate the soft tissue model.

20 Claims, 10 Drawing Sheets

SYSTEMS AND METHODS FOR DESIGN AND MANUFACTURE OF A MODIFIED BONE MODEL INCLUDING AN ACCURATE SOFT TISSUE MODEL

CROSS-REFERENCE TO RELATED APPLICATIONS

This application claims the benefit of U.S. Provisional Patent Application No. 60/787,747, filed on Apr. 1, 2006, which is hereby incorporated by reference for all purposes.

TECHNICAL FIELD

Various embodiments of the present invention generally relate to creation of anatomically correct physical models for an individual patient. More specifically, the embodiments of the present invention relate to systems and methods for design and manufacture of a modified bone model including an accurate soft tissue model.

BACKGROUND

Placement of single or multiple tooth replacement implants has become more common over the last ten years. Surgeons rely on a variety of techniques for both planning and executing the surgery to place these implants. A more contemporary surgical approach is to utilize so called "flapless" surgery, a more minimally-invasive approach to placing dental implants. In this approach, small holes are "punched" through the soft tissue covering the bone of the jaw. The soft tissue of the mouth is commonly referred to as the mucosa. Small holes are punched through the mucosa of the mouth over the area where a dental implant will be placed into bone. Because of the size of the small hole, it is difficult to visualize the bone structure underneath, and to gauge where viable bone may reside. Dentists implanting these implants are thus often left to guess about what lies underneath the soft tissue during these procedures.

Several options exist for giving the dentist some information for bone quality underneath the mucosa. First, many dentists routinely use projection radiographs (x-rays) in the form of panoramic radiographs, lateral cephalometric radiographs or tomographic radiographs for judging bone quality in a specific area. More recently computed tomography and so-called cone-beam computed tomography (or cone-beam volume tomography) has been used to better identify bone shape, quality and quantity in a very specific area.

More recently dentists have relied on physical anatomical models produced using Solid Freeform Fabrication (SFF) techniques (additive fabrication techniques such as stereolithography, fused deposition modeling, three-dimensional printing, selective laser sintering, etc) to evaluate the bone in a very hands-on and tactile way. These models, often referred to as medical models or biomodels, can be used to simulate surgery and plan exactly the position, angulation, depth, etc of the implant. These models are made of the bone and teeth structure, the so called "hard tissue" anatomy of the jaw.

Many of these physical models are now being used to plan dental implant placement and subsequently fabricate a drill-guide that fits onto the patient's bone structure and allows for precise alignment of the drill for placement of the implants. What these anatomical models lack, however, is a representation of the soft tissue of the mouth to allow for creation of a soft tissue borne drill guide that would fit onto the patient's mucosa and provide a guide for "flapless" dental implant surgery.

As such, there are a number of challenges and inefficiencies created in traditional physical models used to plan and/or simulate surgery. For example, the traditional models do not provide a model for the soft tissue. As a result, a great amount uncertainty remains in surgery planning and simulation.

SUMMARY

A method for forming a soft tissue model according to embodiments of the present invention may include receiving medical imaging data representing the facial anatomy of a patient while the patient is wearing a scan prosthesis against the patient's soft tissue, receiving medical imaging data representing the scan prosthesis, and processing the medical imaging data representing the facial anatomy of the patient and the medical imaging data representing the scan prosthesis to generate a three-dimensional model of the patient's facial anatomy and a three-dimensional model of the scan prosthesis. The received medical imaging data may be, for example, computed tomography scan data. A modified hard tissue model of the facial anatomy may be created by adding one or more support structures, such as, for example, pegs, ledges, and/or ridges, to the three-dimensional model of the facial anatomy. A model of the patient's soft tissue may be molded between the three-dimensional model of the scan prosthesis and the modified hard tissue model by pressing the three-dimensional model of the scan prosthesis against the one or more support structures. During the medical imaging of the scan prosthesis and underlying hard tissue, pressure may be applied to the scan prosthesis while the patient is wearing the scan prosthesis to reduce or eliminate any trapped air between the patient's facial anatomy and the scan prosthesis.

A solid freeform fabrication method may be used to create the modified hard tissue model, according to embodiments of the present invention. According to some embodiments of the present invention, the scan prosthesis can be the patient's denture, a copy of a denture, or a provisional denture. The scan prosthesis may include one or more fiducial markers, and the fiducial markers may be used to align the received medical imaging data representing facial anatomy and the received medical imaging data representing the scan prosthesis during the processing of the received medical imaging data. According to some embodiments, the modified hard tissue model includes a representation of an inferior alveolar nerve canal and/or of a mental foramen.

Systems for creating a bone model including an accurate representation of surrounding soft tissue according to embodiments of the present invention may include a scan prosthesis with a recess which fits closely on soft tissue of a patient, a bone model created from medical imaging data of the patient, and one or more support structures added to the bone model or the scan prosthesis. The one or more support structures may be configured to contact the bone model and the scan prosthesis to position the scan prosthesis in a position with respect to the bone model such that a space formed between the recess and the bone model corresponds with a shape of the soft tissue, according to embodiments of the present invention. Such systems according to embodiments of the present invention may further include a formable substrate disposed between the bone model and the scan prosthesis, which may be molded into the shape of the underlying soft tissue between a top half of the mold (scan prosthesis) and a bottom half of the mold (bone model with support structures). According to some embodiments of the present invention, the scan prosthesis is a polymer copy of an existing denture, a provisional denture prosthesis, and/or a bite registration mold. The formable substrate may be a fast curing moldable material such as, for example, silicone putty or urethane putty.

Methods for creating a soft tissue model according to embodiments of the present invention include receiving a first set of medical imaging data representing a combination of the hard tissue facial anatomy of a patient and a scan prosthesis while the patient is wearing the scan prosthesis against soft tissue, receiving a second set of medical imaging data representing the scan prosthesis, processing the second set of medical imaging data to create a virtual three-dimensional model of the scan prosthesis, processing the first and second sets of medical imaging data to create a virtual three-dimensional model of the hard tissue facial anatomy, and creating a modified hard tissue model by adding support structures to the virtual three-dimensional model of the hard tissue facial anatomy. The medical imaging data may be, for example, computed tomography scan data. The support structures may be added to the three-dimensional model of the hard tissue facial anatomy such that placing the virtual three-dimensional model of the scan prosthesis against the support structures results in a space between the modified hard tissue model and the virtual three-dimensional model of the scan prosthesis that is representative of the soft tissue. A solid modified hard tissue model may be formed by rendering the modified hard tissue model in a solid material.

Methods according to such embodiments may further include forming a solid representation of the virtual three-dimensional model of the scan prosthesis, applying a moldable material between the solid modified hard tissue model and the solid representation of the virtual three-dimensional model of the scan prosthesis, and pressing the solid representation of the virtual three-dimensional model of the scan prosthesis onto the solid modified hard tissue model to form the moldable material into the shape of the soft tissue. The solid representation of the virtual three-dimensional model of the scan prosthesis and/or the solid modified hard tissue model may in some cases be formed using a solid freeform fabrication process. Methods according to some other embodiments of the present invention may further include applying a moldable material between the solid modified hard tissue model and the scan prosthesis, and pressing the scan prosthesis onto the solid modified hard tissue model to form the moldable material into the shape of the soft tissue. According to some embodiments of the present invention, the scan prosthesis includes a fiducial marker which may be, for example, a radiographic marker. According to such embodiments, processing the first and second sets of medical imaging data to create the virtual three-dimensional model of the hard tissue facial anatomy may include aligning the first set of medical imaging data with the second set of medical imaging data using the fiducial marker and subtracting the second set of medical imaging data from the first set of medical imaging data. According to some embodiments of the present invention, the scan prosthesis may be an existing denture and/or a provisional denture configured to fit closely with the patient's soft tissue.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 2b illustrates a top view of the exemplary scan prosthesis illustrated in FIG. 2a;

FIG. 3b illustrates a top view of the exemplary physical model of the hard tissue anatomy illustrated in FIG. 3a;

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present invention generally relate to creation of anatomically correct physical models for an individual patient More specifically, embodiments of the present invention relate to systems and methods for design and manufacture of a modified bone model including an accurate soft tissue model.

Some embodiments allow for accurate reproduction of the mucosa by means of visualizing surrounding structures using medical imaging studies. Examples of medical imaging studies include, but are not limited to, computed tomography or cone-beam computed tomography. One embodiment of the present invention allows for the creation of an accurate mucosa model using any moldable material, not just materials that are available for direct production in SFF techniques. From a manufacturing standpoint, this reduces time and cost needed for production of the model.

According to some embodiments, a modified hard tissue model may be created by SFF techniques to incorporate landmarks usable for registration of another object. In some embodiments, the landmarks may be used to register a scan prosthesis.

In one embodiment, the anatomical models include the following: 1) a modified physical model of the bone and teeth structures (hard tissue models); and 2) a physical model of a "scan prosthesis" which the patient was wearing at the time of the scan. In some embodiments, the process may not require replication of a physical copy of the scan prosthesis if the original scan prosthesis is available for use.

One embodiment of the present invention for fabricating accurate anatomical models of the bone and soft tissue may be used to facilitate creation of a drill guide for flapless surgery. Various embodiments for fabricating accurate models include a medical image acquisition process and process for adding extra material to the anatomically accurate bone model to be generated using SFF techniques. The extra material provides a representation of the soft tissue surrounding the bone. In some embodiments, additional representation of other structures (e.g., nerves, nerve canals, mental foramen, etc.) may also be included in the soft tissue and/or otherwise modeled as soft tissue.

In one embodiment, the medical image acquisition process includes imaging accurate models of the anatomy and the scan prosthesis with a total of two or more medical imaging scans. According to some embodiments of the present invention, medical imaging includes contact or non-contact digitizing technology, such as laser scanning or photogrammetry-based scanning. The medical image acquisition process provides data showing a true representation of the space occupied by mucosa, or soft tissue of the mouth.

A process for adding extra material to the anatomically accurate bone model to be generated using SFF techniques may be used in one embodiment. The extra material may be designed digitally and then added to the bone model to allow for registration of the scan prosthesis on top of the bony anatomy. The registration of the bony anatomy with the scan prosthesis creates a gap which represents the mucosa of the patient, given that the scan prosthesis is tight fitting according to some embodiments.

Some embodiments include a production of a modified hard tissue model produced by SFF techniques that allows the hard tissue model to relate to the scan prosthesis or a copy of the scan prosthesis, leaving a void where the mucosa resides. This technique allows for accurate modeling of the mucosa overlaid on accurate bone structure models produced from medical imaging studies such as CT or cone-beam CT. Molding of the mucosa within the mold cavities created by the hard tissue model created with SFF techniques in combination with the scan prosthesis can be accomplished in any moldable material. The fact that the mucosa model is not limited to materials that can be directly produced by SFF techniques is an advantage of some embodiments of the present invention.

Modeling of the mucosa in a non-rigid material to simulate the soft tissue of the mouth is possible because of the ability to use any available moldable material. Methods according to embodiments of the present invention give a modeler the ability to produce a single set of models (i.e., a hard tissue model and a copy of the scan prosthesis if it is not available), without a need to make a "master" model or print out a special "mold" of the mucosa. By producing a single set of models there is a decrease in manufacturing cost and time needed for modeling of these structures.

In the following description, for the purposes of explanation, numerous specific details are set forth in order to provide a thorough understanding of embodiments of the present invention. It will be apparent, however, to one skilled in the art that embodiments of the present invention may be practiced without some of these specific details.

Embodiments of the present invention may be provided as a computer program product which may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

While, for convenience, embodiments of the present invention are described with reference to fabricating accurate anatomical models of the bone and soft tissue in the facial anatomy of a patient (e.g., patient's mouth), embodiments of the present invention are equally applicable to various other bones and soft tissue of the patient.

As used herein, the terms "connected" or "coupled" and related terms are used in an operational sense and are not necessarily limited to a direct physical connection or coupling. Thus, for example, two devices or structures may be coupled directly, or via one or more intermediary media, structures, or devices. As another example, devices may be coupled in such a way that information can be passed therebetween, while not sharing any physical connection with one another. Based on the disclosure provided herein, one of ordinary skill in the art will appreciate a variety of ways in which connection or coupling exists.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phases do not necessarily refer to the same embodiment.

If the specification states a component or feature "may", "can", "could", or "might" be included or have a characteristic, that particular component or feature is not required to be included or have the characteristic.

The term "model" generally refers to a representation, visualization, approximation, imitation, or emulation of a structure, formation, device, or other physical object. According to various embodiments, a model may be a physical model or a virtual model. A model may include all or only some of the features present in the structure, formation, device, or physical object that the model is representing. Moreover, a model may provide an accurate representation of some features, while only an approximation of others. In some cases, a model may not represent certain features at all. In some embodiments, a model may be miniaturized version, a true scaled version, or an enlarged version of the structure, formation, device, or physical object that the model represents. The term "responsive" includes completely and partially responsive.

Figure 1:
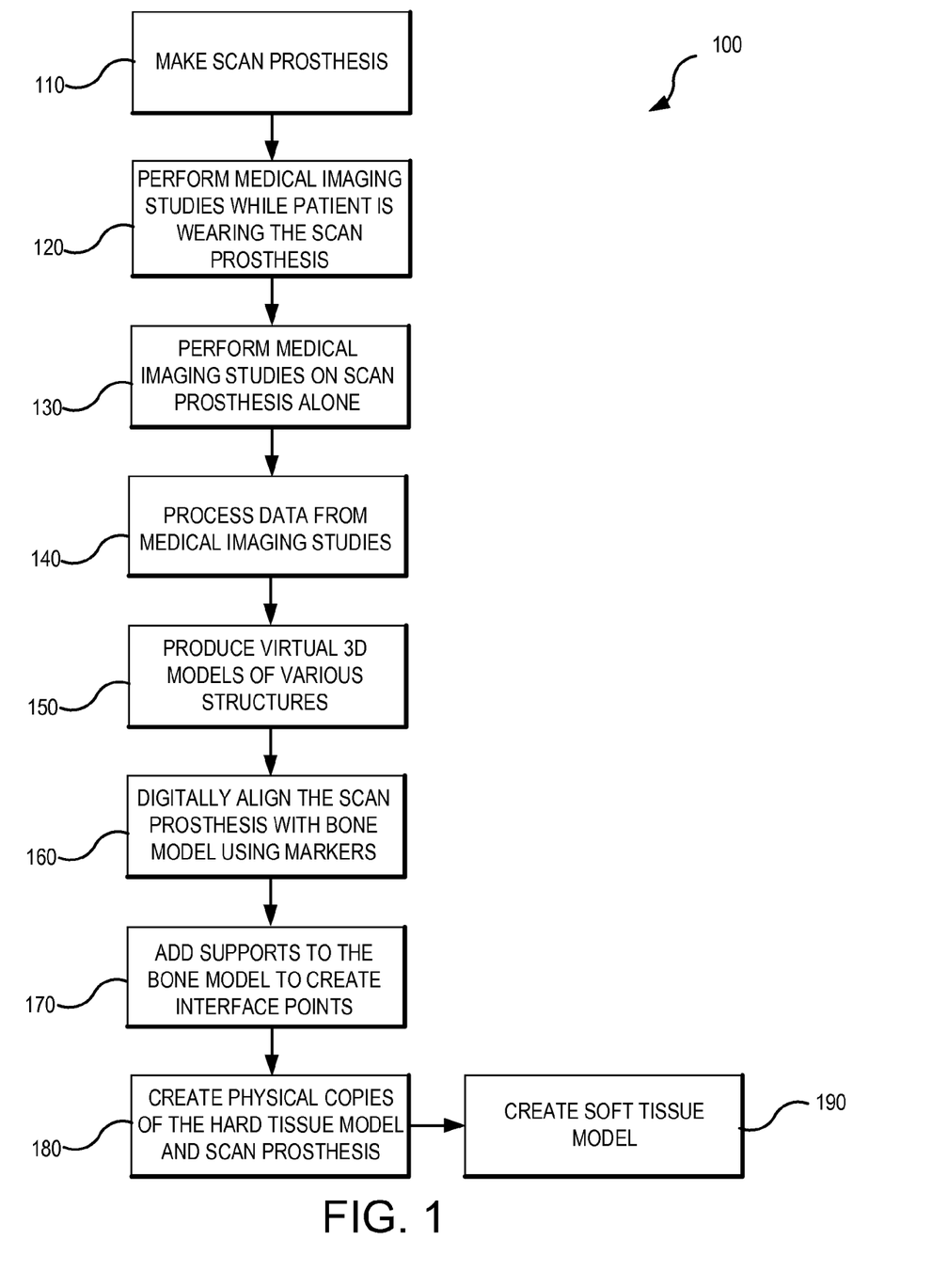
FIG. 1 is a flow chart representing an exemplary algorithm for creating a modified bone model that includes an accurate representation of the soft tissue surrounding the bone, in accordance with one or more embodiments of the present invention.

FIG. 1 is a flow chart representing an exemplary algorithm 100 for creating a modified bone model that includes an accurate representation of the soft tissue surrounding the bone. According to one embodiment, a scan prosthesis is made in step 110. The scan prosthesis is made prior to a patient's medical imaging study in order to help accurately image the mucosa space in the mouth, according to embodiments of the present invention. The scan prosthesis may also be an existing mouth implement, such as, for example, a denture. Ideally, the inside surface of the scan prosthesis conforms to the soft tissue against which the scan prosthesis is placed. Further, the scan prosthesis may be held firmly against the soft tissue during medical imaging studies in order to evacuate any air that may exist between the scan prosthesis and the soft tissue. The medical imaging study may be, but is not limited to, a computed tomography (CT) scan or cone-beam CT scan. In one embodiment, the scan prosthesis is worn during the medical imaging study. According to one embodiment, if the patient is fully edentulous (i.e., has no teeth on one arch) the scan prosthesis can be a copy of the patient's existing denture or the denture itself.

The scan prosthesis can be, but is not limited to, the following: a) a polymer facsimile model of a patient's existing denture, b) a polymer model of a provisional or temporary denture prosthesis, c) a bite registration made of wax, acrylic or some other moldable material, or d) some combination of the other three a) through c). In some embodiments, the scan prosthesis has discrete fiducial markers. Such fiducial markers may be, for example, radiopaque and/or radiographic markers in place for later registration. Examples of these markers include, but are not limited to, small amounts of gutta percha material, small metallic objects or other radiopaque elements commonly used for registration and/or alignment of two datasets.

According to one embodiment, medical imaging studies are performed on a particular patient's facial anatomy in step 120. Examples of medical imaging studies include, but are not limited to, computed tomography, cone-beam computed tomography, and magnetic resonance imaging. In accordance with one embodiment, the patient wears the scan prosthesis during the scan and applies adequate pressure to ensure proper fit and reduce the possibility of trapped air between the patient's anatomy and the scan prosthesis.

After the patient goes through medical imaging studies in step 120, medical imaging studies are then performed on the scan prosthesis alone in step 130. According to various embodiments, if a scan prosthesis exists for both the upper and lower arches, each scan prosthesis may include radiopaque markers and each scan prosthesis may be scanned separately. In some embodiments, scanning the prosthesis may be accomplished with the scan prosthesis alone or may involve imaging a copy of the patient's dental anatomy, a dental cast, along with the scan prosthesis.

Data from the medical imaging studies is processed in step 140. The data from the medical imaging studies can be processed with data segmentation software in accordance with one or more embodiments. Using such software, virtual three-dimensional models can be produced in step 150. In accordance with various embodiments, virtual three-dimensional models of one or more of the following structures can be created: a) hard tissue of the patient's upper and/or lower jaw (maxilla and mandible); b) fiducial markers from the patient's CT; c) fiducial markers from the scan prosthesis CT; d) the scan prosthesis; and e) mucosa. In one embodiment, the scan prosthesis is digitally aligned with the patient's bone models in step 160. According to some embodiments of the present invention, the virtual three-dimensional model of the hard tissue may be created by aligning (using the fiducial markers) the model of the scan prosthesis with the model of the patient's anatomy while wearing the scan prosthesis, and then subtracting the data points representing the scan prosthesis from the data points representing the combination of the scan prosthesis and the underlying hard tissue structure. In some embodiments, the digital alignment may occur via alignment of the fiducial markers from the scan prosthesis CT to the fiducial markers in the patient CT.

In some embodiments, the virtual three-dimensional design software can be used to add "supports" (e.g., ledges, bases, pegs, etc) to the bone model in step 170. In one embodiment, the supports are added at the upper edges (for upper jaw) or lower edges (for lower jaw) of the bone model to create interface points between the support and the scan prosthesis. The supports may be geometric or free-form in shape, as long as they create sufficient surfaces to reliably sustain the position of the scan prosthesis on the bone model. In some embodiments, more than one support may be added. Two to ten supports may be beneficial for adequate stability of the scan prosthesis on the hard tissue model in some embodiments. One purpose of these support structures is to create a physical "space" between the two models, where such space corresponds with space occupied by soft tissue in the patient's medical imaging study. The hard tissue model with extra supports added may be referred to as the modified hard tissue model.

In some embodiments, Solid Freeform Fabrication (SFF) technology may be used in step 180 to create physical copies of the modified hard tissue model and the scan prosthesis, created as two separate pieces. According to various embodiments, the modified hard tissue model and the scan prosthesis model may be made in a translucent or opaque material that is hard or soft or somewhere in between. In one embodiment, if the original scan prosthesis is available, reproduced copies of the scan prosthesis may not be necessary.

Step 190 in exemplary algorithm 100 involves creation of an accurate soft tissue mucosa model, according to one or more embodiments of the present invention. In some cases, the soft tissue model may be preferred in a soft material. However, in some applications it may be more desirable for the mucosa model to be created in a hard material. In one embodiment, the creation of the soft tissue mucosa model is done by pressing a malleable material (such as silicone putty, urethane putty, or any fast-curing moldable material) into the recess of the scan prosthesis, copy of the scan prosthesis, or edentulous ridge of the modified bone model. Manual pressure may then be applied to the models until the scan prosthesis comes in contact with all support structures. If enough malleable material has been added and the support structures from the modified bone model come into contact with the scan prosthesis then the created model accurately depicts the space left between the scan prosthesis and the patient's hard tissue structures, which corrresponds to the patient's soft tissue.

In one embodiment, a virtual model of the mucosa can be created using the virtual three-dimensional design software. The virtual model of the mucosa can be created according to various embodiments by aligning the data for the scan prosthesis and the data from the medical imaging study of the patient wearing the scan prosthesis, and recreating the shape of the gap (corresponding to the mucosa) between the scan prosthesis and the underlying hard tissue. Design software may be used to create such a virtual representation of the mucosa by recreating the scanned shape of the space between the scan prosthesis and the underlying hard tissue. According to some embodiments of the present invention, the soft tissue mucosa model may be formed by directly printing the virtual three-dimensional soft tissue model using techniques such as SFF and others. This direct printing or direct rendering of the mucosa model may be done instead of, or in addition to, formation of a mucosa model through a molding process between the mold top half (scan prosthesis or copy thereof) and the mold bottom half (modified hard tissue model), according to embodiments of the present invention.

Figure 2A:
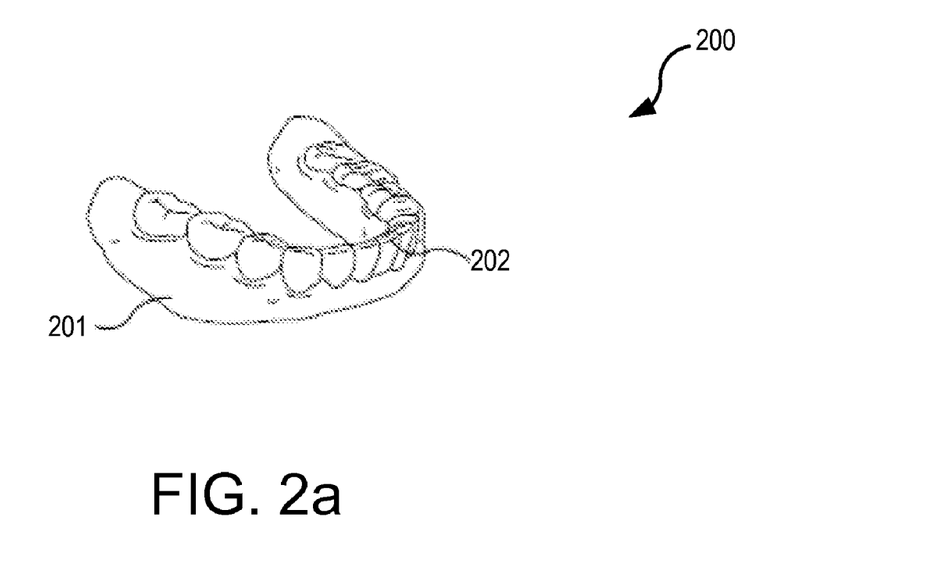
FIG. 2a illustrates a front perspective view of an exemplary scan prosthesis in accordance with one or more embodiments of the present invention.
Figure 2B:
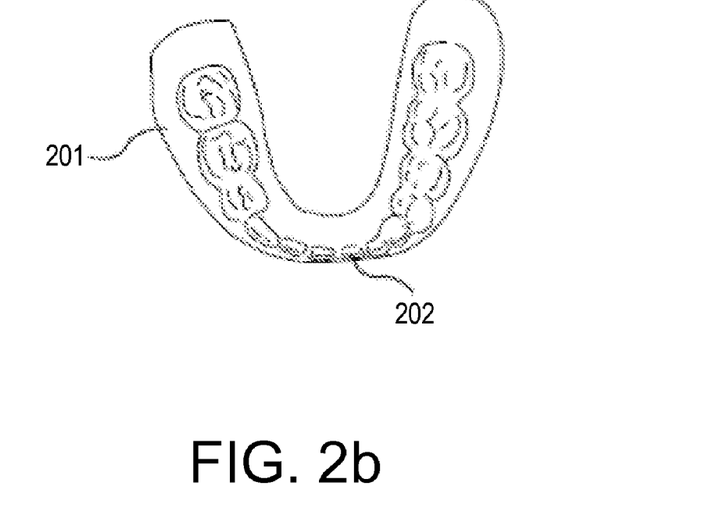

FIG. 2a illustrates a front perspective view of an exemplary scan prosthesis 200 in accordance with one or more embodiments of the present invention. FIG. 2b illustrates a top view of the exemplary scan prosthesis 200 illustrated in FIG. 2a. Scan prosthesis 200 is a copy of a denture or a "provisional" prosthesis, in some embodiments of the present invention. According to various embodiments, scan prosthesis 200 can be made by a dentist or by someone else. According to various embodiments, scan prosthesis 200 may be made in some formable material such as, for example, clay, putty, and/or polymer.

In the embodiment shown, scan prosthesis 200 is a copy of a provisional or temporary denture worn by the patient after dental implant surgery. In addition, the representation of teeth 202 in this model may accurately represent the appearance of final tooth restoration. Although the scan prosthesis 200 is depicted with a particular outer structure according to embodiments of the present invention, a more significant feature of the scan prosthesis 200 is the shape of the recess in the scan prosthesis 200 which interfaces with the patient's soft tissue. The closer the fit between the inside of the scan prosthesis (e.g. the recess) and the patient's soft tissue, the more accurate the creation of the soft tissue model according to embodiments of the present invention. A denture or provisional denture may conveniently be used as a scan prosthesis 200 according to embodiments of the present invention because it has already been formed to fit snugly against a patient's soft tissue. In some embodiments, several fiducial markers for later alignment of two different datasets may be integrated into the scan prosthesis 200.

Figure 3A:
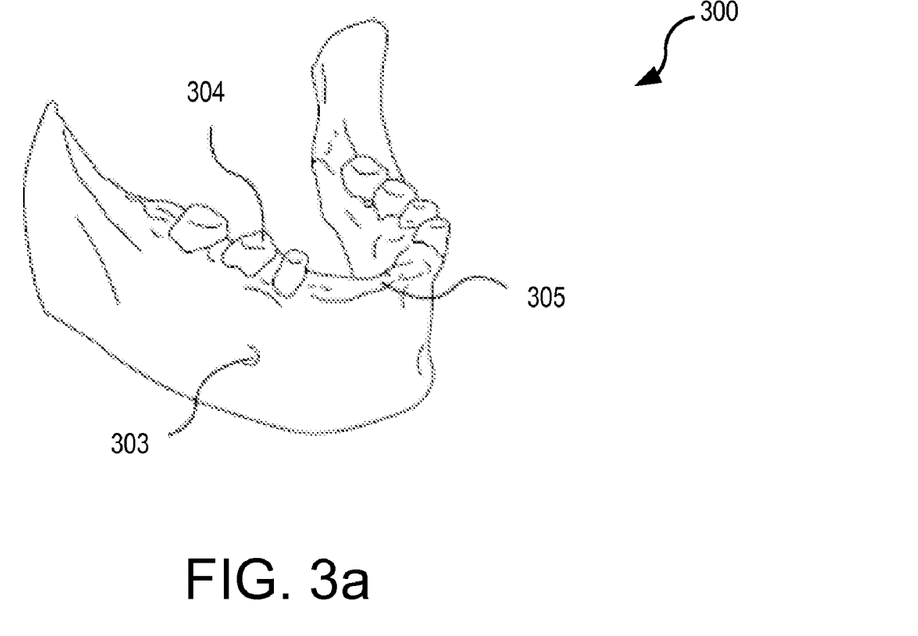
FIG. 3a illustrates a front perspective view of an exemplary physical model of the hard tissue anatomy of a patient in accordance with some embodiments of the present invention.
Figure 3B:
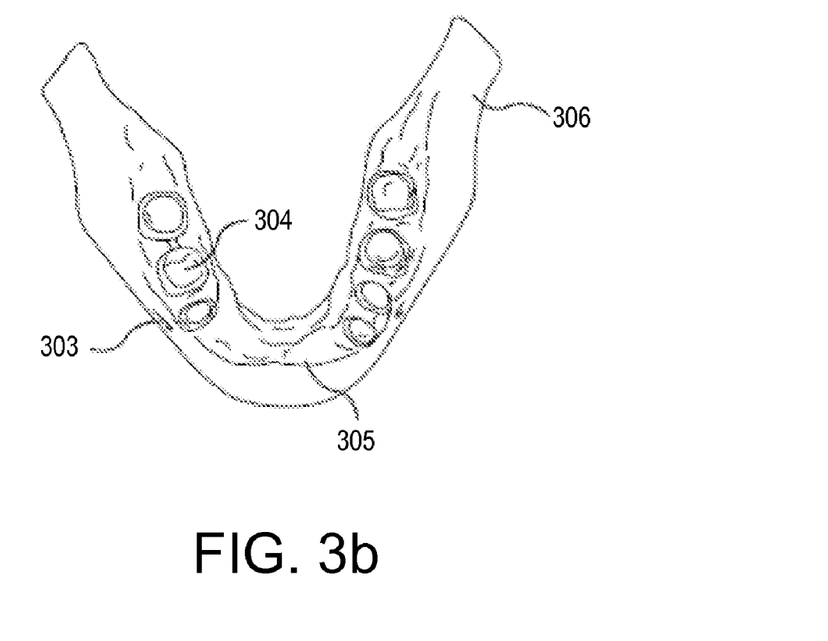

FIG. 3a illustrates a front perspective view of an exemplary physical model 300 of the hard tissue anatomy of a patient in accordance with some embodiments of the present invention. FIG. 3b illustrates a top view of the exemplary physical model 300. The physical model 300 represents the hard tissue anatomy of a patient. In particular, physical model 300 shows mandibular bone structure and a few existing posterior mandibular teeth. Physical model 300 accurately represents the patient's anatomy and includes visualization of vital features and structures such as the inferior alveolar nerve canal and mental foramen. Physical model 300 may be created, according to one embodiment, using medical image data from one or more medical imaging studies. In one embodiment, physical model 300 can be made by SFF techniques and the medical image data.

FIGS. 3a-3b include a detail of the mandibular bone model 300 showing the mental foramen 303, the exit point for the mental nerve that travels through the mandible and out to the lip and chin. The example patient on which the bone model 300 is based has some existing teeth such as existing molar 304. The example patient is also missing teeth in the anterior portion of the mandible, as evidenced by the lack of teeth leaving just a bony ridge 305. The ramus 306 of the mandibular bone model, as created by SFF techniques and based on medical imaging data, is also shown in FIG. 3b, according to embodiments of the present invention.

Figure 4A:
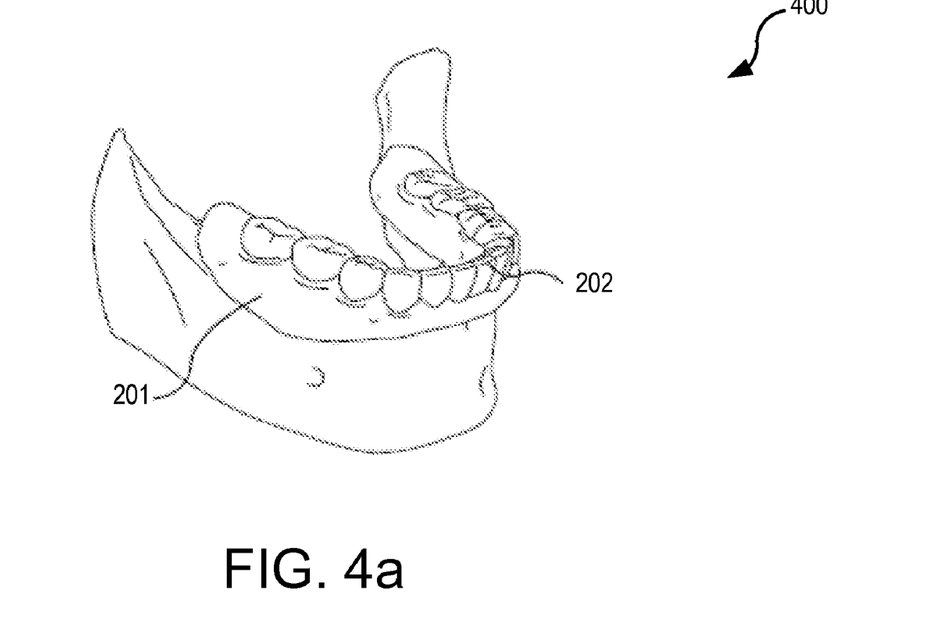
FIG. 4a illustrates a front perspective view of an exemplary scan prosthesis and exemplary physical model combined in accordance with one or more embodiments of the present invention.
Figure 4B:
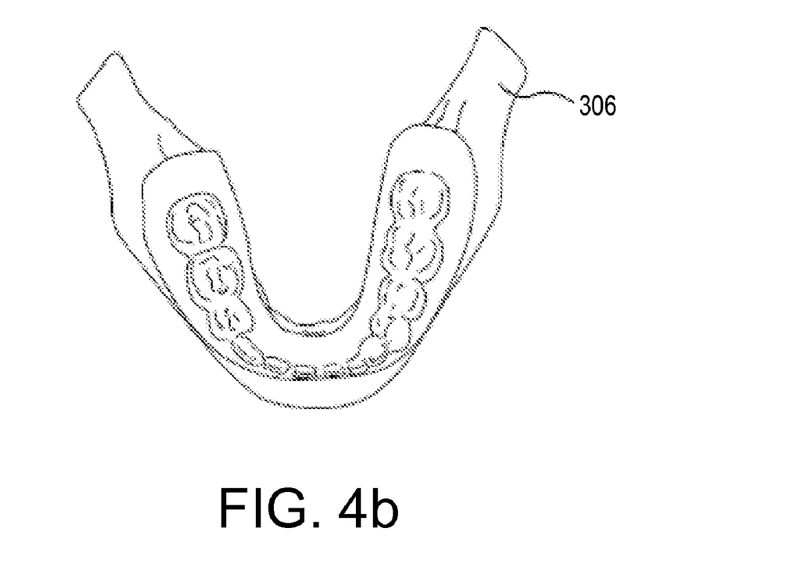
FIG. 4b illustrates a top view of the combined exemplary scan prosthesis and exemplary physical model of FIG. 4a in accordance with one or more embodiments of the present invention.

FIG. 4a illustrates a front perspective view of a combined model 400 of scan prosthesis 200 and physical model 300 in accordance with one or more embodiments of the present invention. FIG. 4b is a top view of the combined model 400 in accordance with one or more embodiments of the present invention. As previously discussed, the physical models of scan prosthesis 200 and physical model 300 can be created by using medical imaging data and SFF techniques. While the combined model 400 accurately depicts the scan prosthesis 200 and the hard tissue model 300, simply placing the scan prosthesis 200 over the hard tissue model 300 does not lead to an accurate distance between the models 200, 300 representative of the soft tissue therebetween.

Figure 5A:
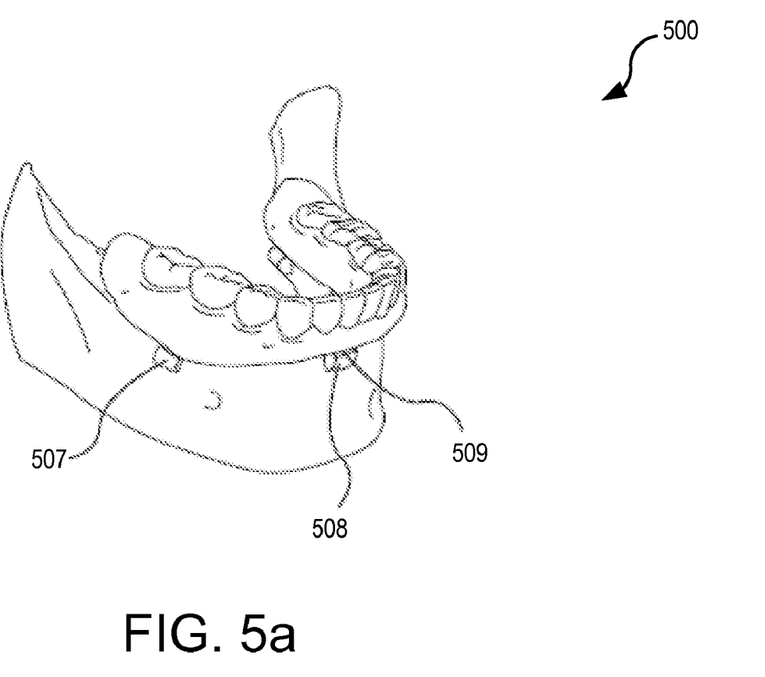
FIG. 5a illustrates a front perspective view of physical models of a scan prosthesis and a bone structure of a mandible with small pegs in accordance with various embodiments of the present invention.
Figure 5B:
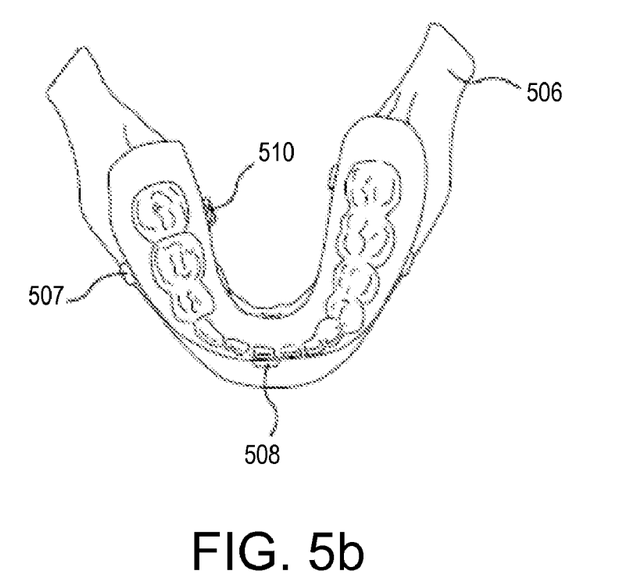
FIG. 5b illustrates a top view of the physical models of FIG. 5a in accordance with various embodiments of the present invention.

FIGS. 5a-5b represent different views of an exemplary embodiment of physical models of a scan prosthesis and a bone structure of the mandible with small pegs 507, 508, 510. According to one embodiment, the physical models may be the same physical models described in FIGS. 3a-3b and 4a-4b to which small "pegs" 507, 508, and 510 have been added. Pegs 507, 508, 510 allow the scan prosthesis to rest in the "as-scanned" position above the bone structure of the mandible, in accordance with one or more embodiments of the present invention.

Pegs 507, 508, and 510 are examples of a geometric shape added to the physical bone model to allow for proper positioning of the scan prosthesis. The geometric shape of pegs 507, 508, 510 may be any shape as long as a horizontal or substantially horizontal surface of the pegs 507, 508, 510 is created to match with a surface of the scan prosthesis. In the embodiment shown, peg 507 has been added buccally and laterally, but may be added anywhere to create a stable "shelf" on which the scan prosthesis may rest. In addition to peg 507, peg 508 has been added buccally and anteriorly. Peg 510 has been added on the lingual area to help create a stable shelf for the scan prosthesis to rest. FIG. 5a also shows an exemplary interface point 509 between a bone model peg 508 and the scan prosthesis. Interface point 509 provides a firm and tight tolerance fit between the two separate physical objects. Although the pegs 507, 508, 510 are described herein as being added to the physical bone model (e.g. the hard tissue model 300), according to alternative embodiments of the present invention, pegs, ledges, and/or ridges may be added to either the hard tissue model 300, the scan prosthesis or scan prosthesis model 200, or both.

One advantage of the small pegs 507, 508, and 510 is that they create a void between the two models (e.g., the scan prosthesis 200 and physical bone model 300) that accurately describes these structures as they were imaged by medical imaging techniques. In the embodiment shown in FIGS. 5a-5b, five pegs have been added to the bone model, two lingually and three buccally, creating a stable base. In other embodiments, more or less pegs may be used in the same or different locations. The pegs may be designed and placed onto a virtual representation of the hard tissue model 300 to form a modified bone model; the modified bone model may then later be molded or printed using solid freeform fabrication, according to embodiments of the present invention. Alternatively, the pegs may be added to a physical hard tissue model 300 which has already been molded in a solid material. Still yet, in some embodiments, other geometric formations such as ridges, ledges, bases, and the like may be used to stabilize the scan prosthesis 200 as it interfaces with the underlying bone model 300, such that the geometry of the space between the scan prosthesis 200 and the underlying bone model 300 closely represents the geometry of the space between the scan prosthesis and the patient's underlying bone as detected by medical imaging studies.

Figure 6A:
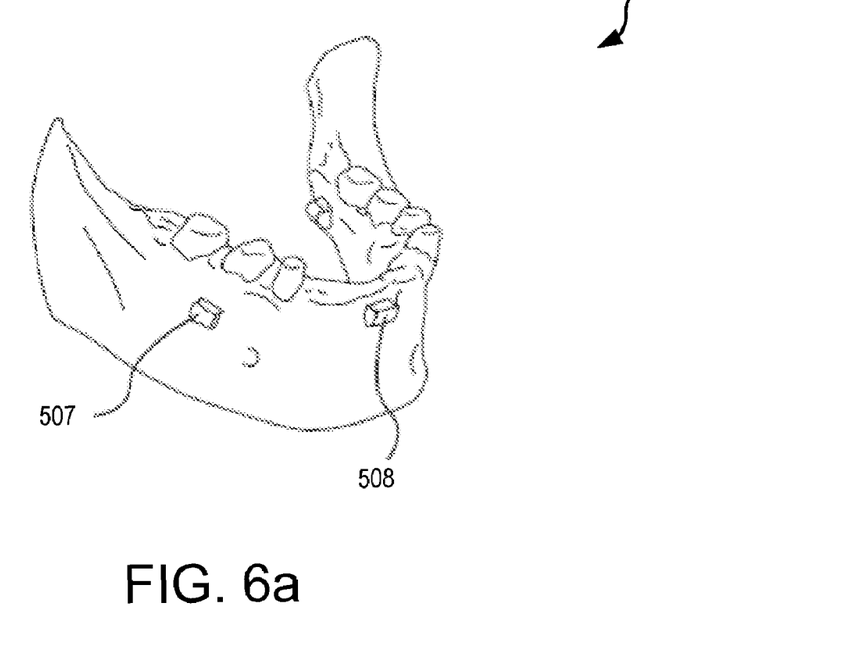
FIG. 6a illustrates a front perspective view of a mandibular model with pegs in accordance with one or more embodiments of the present invention.
Figure 6B:
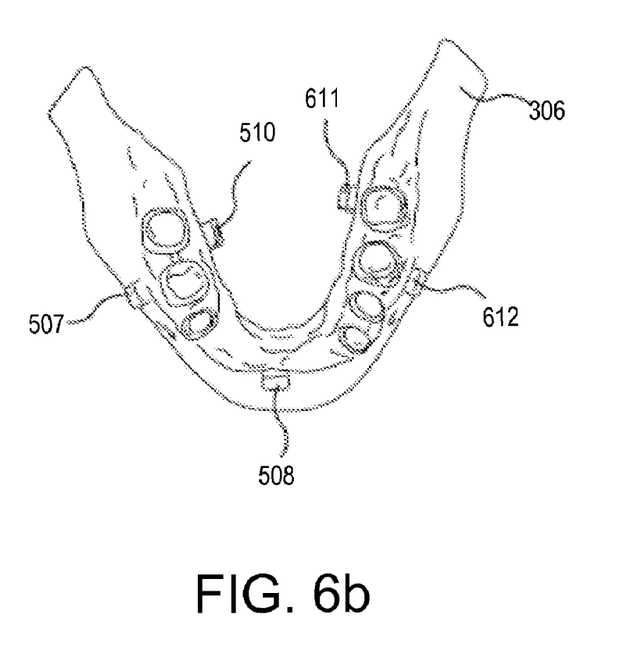
FIG. 6b illustrates a top view of the mandibular model with pegs of FIG. 6a, in accordance with one or more embodiments of the present invention.

FIGS. 6a and 6b illustrate two views of a mandibular model 600 with pegs in accordance with one or more embodiments of the present invention. FIG. 6a is a front perspective view of the mandibular model of FIGS. 5a and 5b for visualization of the pegs that may be added to the bone model according to embodiments of the present invention. Pegs 611 and 612 are examples of geometric shapes added to the physical bone model to allow for proper positioning of the scan prosthesis 200. Peg 611 has been added on the lingual area. Peg 612 has been added buccally and laterally. However, in other embodiments, these pegs can be added anywhere to create a stable shelf or support on which the scan prosthesis 200 rests and/or against which the scan prosthesis 200 may be pressed during molding of the mucosa model.

Figure 7A:
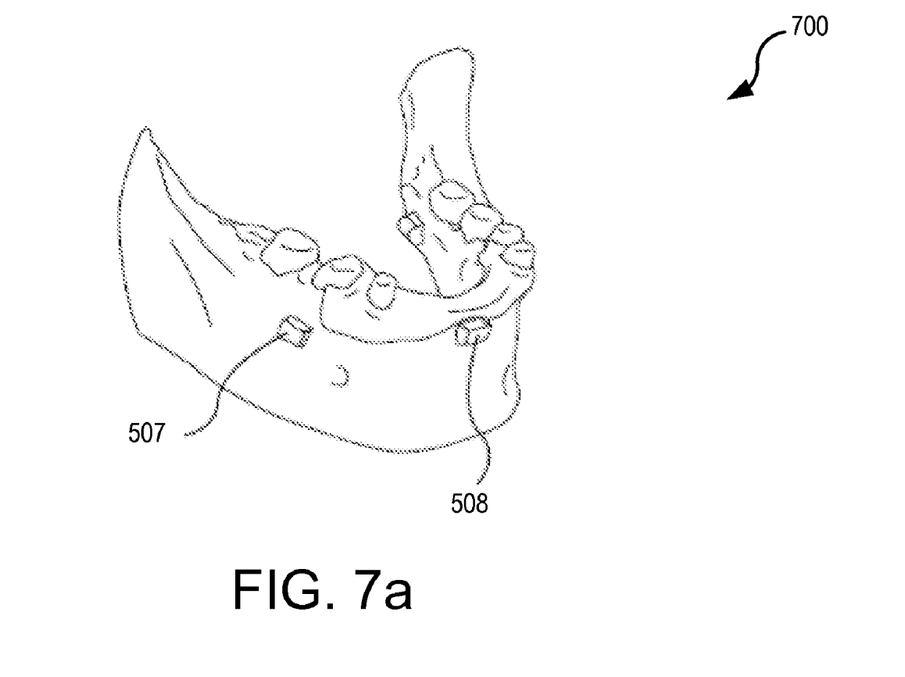
FIG. 7a illustrates a front perspective view of a mandibular model with an overlay of mucosa tissue in the anterior, edentulous section of the mandible in accordance with some embodiments of the present invention.
Figure 7B:
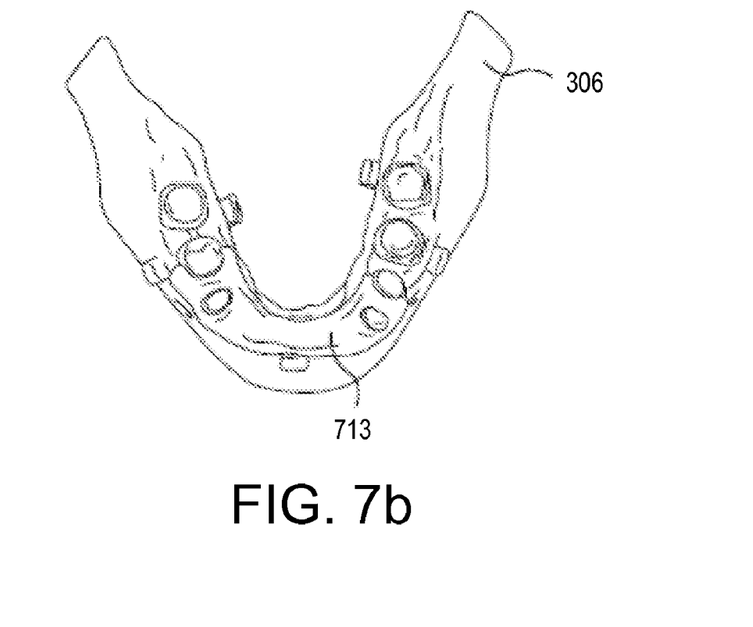
FIG. 7b illustrates a top view of the mandibular model of FIG. 7a, in accordance with some embodiments of the present invention.

FIGS. 7a-7b illustrate different views of a mandibular model 700 with an overlay of mucosa tissue in the anterior, edentulous section of the mandible in accordance with some embodiments of the present invention. According to various embodiments, the mandibular model 700 may be created by SFF techniques and based on medical imaging for a specific patient with an overlay of mucosa tissue in the anterior, edentulous section of the mandible.

According to various embodiments, a physical model of the mucosa 713 is molded by taking a moldable material and sandwiching it between the physical bone model and the physical scan prosthesis. In the embodiment shown, for example, the mucosa overlay is created by sandwiching or compressing a moldable material between the mandibular model 300 and the related scan prosthesis 200. The pegs described above serve to maintain alignment and hold space for the mucosa to be molded, in accordance with one or more embodiments of the present invention. This process creates an accurate model of the medical image data with the aid of the pegs added to the bone model.

In some embodiments, mucosa modeling is desired only for the patient's local anatomy where dental implants will be placed. In such cases, as shown in the embodiment of FIGS. 7a-7b, mucosa modeling may be confined to such local anatomy, such as, for example, the anterior portion of the maxilla.

Figure 8A:
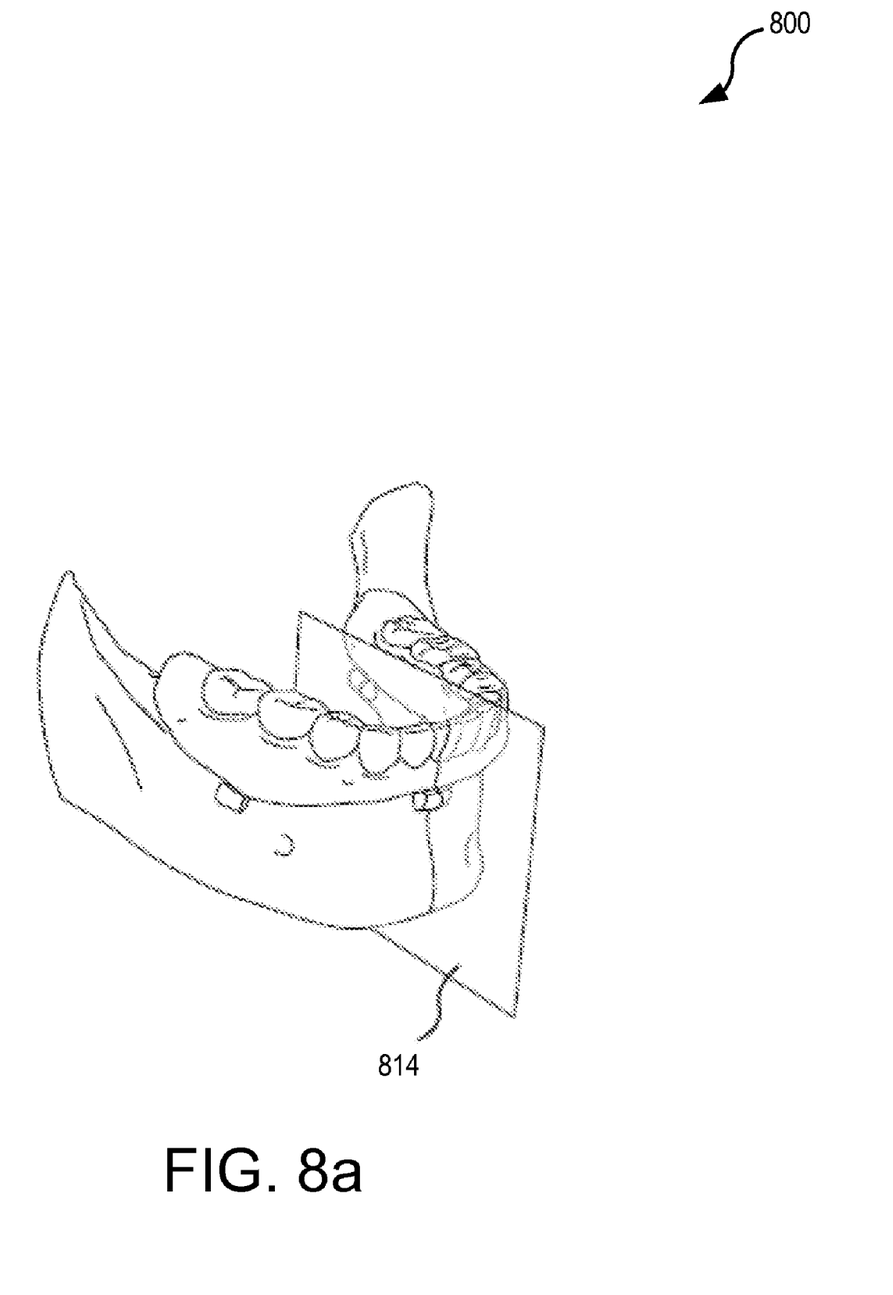
FIG. 8a illustrates an exemplary mandibular model with a plane inserted in the sagittal plane for visualization purposes, in accordance with one or more embodiments of the present invention.
Figure 8B:
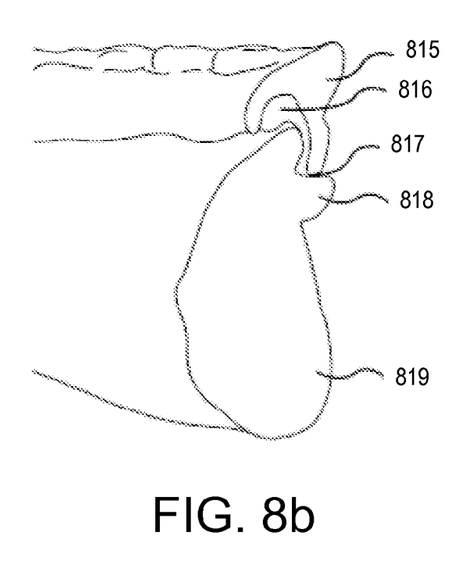
FIG. 8b illustrates a cross-sectional view of the exemplary mandibular model of FIG. 8a taken along plane 814 of FIG. 8a in accordance with one or more embodiments of the present invention.
Figure 8C:
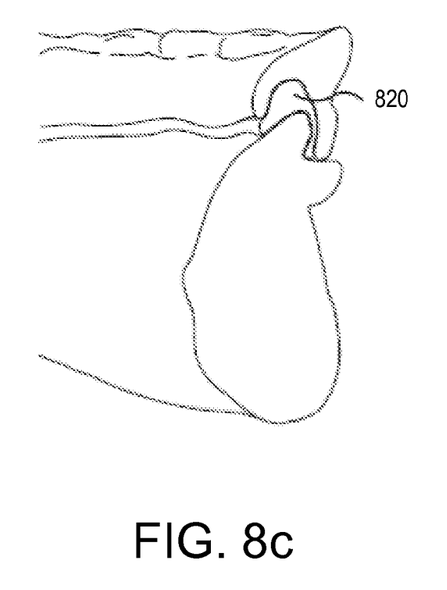
FIG. 8c illustrates a cross-sectional view of the exemplary mandibular model of FIGS. 8a and 8b taken along plane 814 of FIG. 8a in accordance with one or more embodiments of the present invention.

FIG. 8a illustrates an exemplary mandibular model 800 with a plane 814 depicted in the sagittal plane for visualization purposes. According to one embodiment, mandibular model 800 is created by SFF techniques and is based on medical imaging for a specific patient. FIGS. 8b-8c depict cross sectional views of the mandibular model 800 taken along plane 814 of FIG. 8a. These cross sectional views illustrate the bone structure (bottom), the scan prosthesis (top) and a gap left in between representing the mucosa space. Peg 818 serves to hold the scan prosthesis in proper position three-dimensionally, creating an accurate representation of the mucosa between the bone model and the scan prosthesis as observed by medical imaging techniques. The cross sectional views of the scan prosthesis show the proposed tooth occlusal surface 815. Gap 816 created between the physical bone model and the physical scan prosthesis model can also be seen in the embodiment illustrated by FIGS. 8b-8c. This gap is the mucosa for the depicted anatomical model of the patient.

Cross sectional view 8b also illustrates a tight interface 817 between the scan prosthesis and the physical bone model. The peg 818 creates a stable surface for the scan prosthesis to rest on top of and to hold the proper position of the mucosa.

Some embodiments of the present invention include a bone model 819 with information on vital structures such as blood vessels, nerve structures, existing teeth and impacted teeth within the model in the same or a different color. FIG. 8c depicts a cross sectional view showing the mucosa space 820 as provided through medical imaging of the patient and the scan prosthesis.

Figure 9:
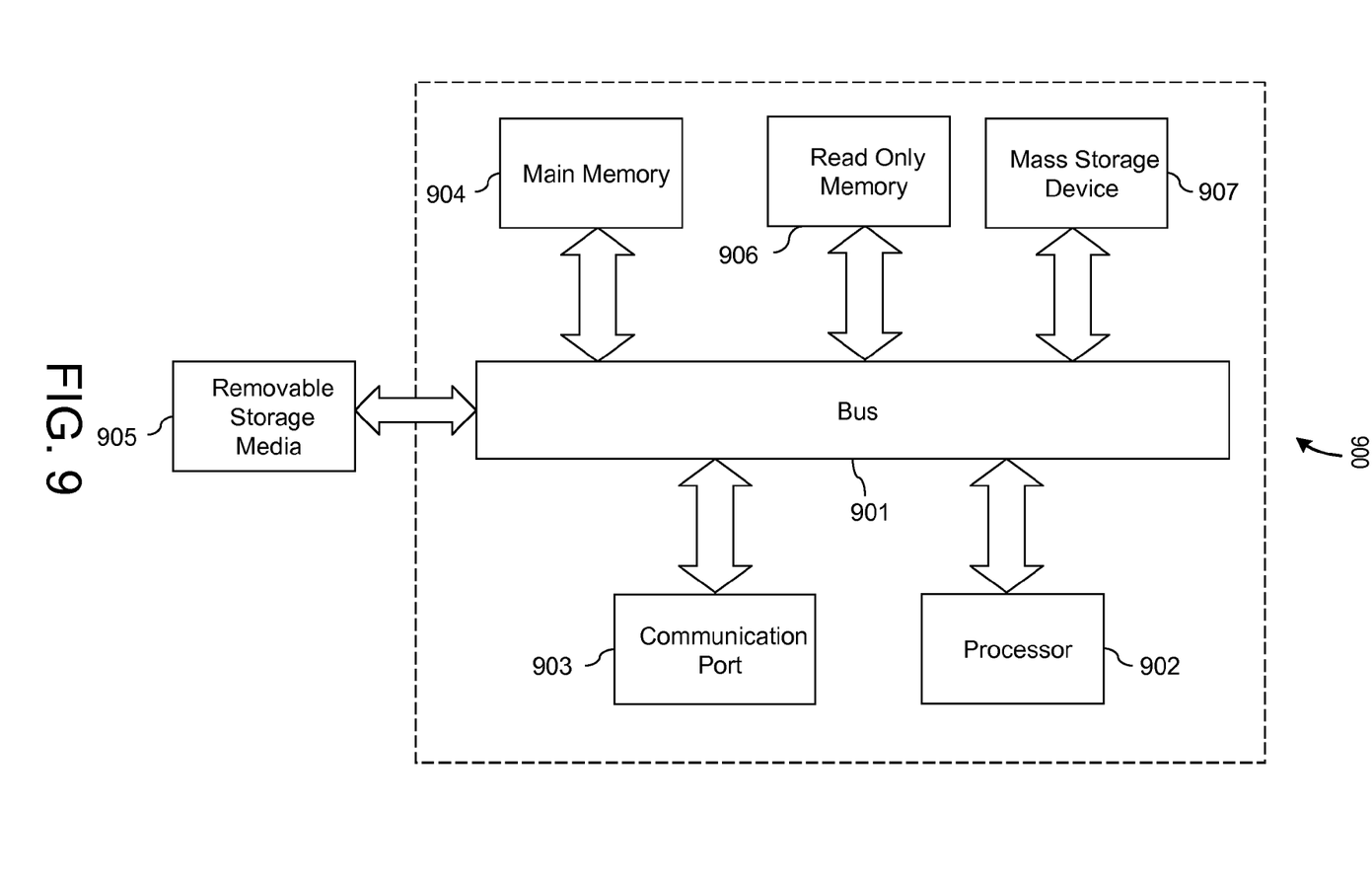
FIG. 9 illustrates an example of a computer system with which embodiments of the present invention may be utilized.

Embodiments of the present invention include various steps that may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 9 is an example of a computer system 900 with which embodiments of the present invention may be utilized. According to the present example, the computer system includes a bus 901, at least one processor 902, at least one communication port 903, a main memory 904, a removable storage media 905, a read only memory 906, and a mass storage 907.

Processor(s) 902 can be any known processor, such as, but not limited to, an Intel® Itanium® or Itanium 2® processor(s), or AMD® Opteron® or Athlon MP® processor(s), or Motorola® lines of processors. Communication port(s) 903 can be any of an RS-232 port for use with a modem based dialup connection, a 10/100 Ethernet port, or a Gigabit port using copper or fiber. Communication port(s) 903 may be chosen depending on a network such a Local Area Network (LAN), Wide Area Network (WAN), or any network to which the computer system 900 connects.

Main memory 904 can be Random Access Memory (RAM), or any other dynamic storage device(s) commonly known in the art. Read only memory 906 can be any static storage device(s) such as Programmable Read Only Memory (PROM) chips for storing static information such as instructions for processor 902. Mass storage 907 can be used to store information and instructions. For example, hard disks such as the Adaptec® family of SCSI drives, an optical disc, an array of disks such as RAID, such as the Adaptec family of RAID drives, or any other mass storage devices may be used.

Bus 901 communicatively couples processor(s) 902 with the other memory, storage and communication blocks. Bus 901 can be a PCI/PCI-X or SCSI based system bus depending on the storage devices used. Removable storage media 905 can be any kind of external hard-drives, floppy drives, IOMEGA® Zip Drives, Compact Disc-Read Only Memory (CD-ROM), Compact Disc-Re-Writable (CD-RW), Digital Video Disk-Read Only Memory (DVD-ROM). The components described above are meant to exemplify some types of possibilities. In no way should the aforementioned examples limit the scope of the invention, as they are only exemplary embodiments.

In conclusion, the present invention provides novel systems, methods and arrangements for design and manufacture of a modified bone model including an accurate soft tissue model. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method comprising:
    receiving medical imaging data representing facial anatomy of a patient while the patient is wearing a scan prosthesis against the patient's soft tissue;
    receiving medical imaging data representing the scan prosthesis;
    processing the medical imaging data representing the facial anatomy of the patient and the medical imaging data representing the scan prosthesis to generate a three-dimensional model of the facial anatomy and a three-dimensional model of the scan prosthesis;
    creating a modified hard tissue model of the facial anatomy by adding one or more support structures to the three-dimensional model of the facial anatomy; and
    molding a model of the patient's soft tissue between the three-dimensional model of the scan prosthesis and the modified hard tissue model by pressing the three-dimensional model of the scan prosthesis against the one or more support structures.

2. The method of claim 1, further comprising applying pressure to the scan prosthesis while the patient is wearing the scan prosthesis to reduce or eliminate any trapped air between the facial anatomy and the scan prosthesis.

3. The method of claim 1, wherein the one or more support structures include one or more ridges.

4. The method of claim 1, wherein creating the modified hard tissue model comprises creating the modified hard tissue model with a solid freeform fabrication method.

5. The method of claim 1, wherein the scan prosthesis is a copy of a provisional denture.

6. The method of claim 1, wherein the scan prosthesis includes one or more fiducial markers, the method further comprising using the fiducial markers to align the received medical imaging data representing facial anatomy and the received medical imaging data representing the scan prosthesis during the processing of the received medical imaging data.

7. The method of claim 1, wherein the modified hard tissue model includes a representation of an inferior alveolar nerve canal and of a mental foramen.

8. The method of claim 1, wherein the medical image data representing the facial anatomy comprises computed tomography scan data.

9. A system for creating a bone model including an accurate representation of surrounding soft tissue, the system comprising:
    a scan prosthesis including a recess, the recess fitting closely on soft tissue of a patient;
    a bone model created from medical imaging data of the patient;
    one or more support structures added to the bone model or the scan prosthesis, the one or more support structures configured to contact the bone model and the scan prosthesis to position the scan prosthesis in a position with respect to the bone model such that a space formed between the recess and the bone model corresponds with a shape of the soft tissue; and
    a formable substrate disposed between the bone model and the scan prosthesis.

10. The system of claim 9, wherein the scan prosthesis is a polymer copy of an item selected from the group consisting of: an existing denture, a provisional denture prosthesis, and a bite registration mold.

11. The system of claim 9, wherein the formable substrate is a fast curing moldable material selected from the group consisting of: silicone putty and urethane putty.

12. A method for creating a soft tissue model, the method comprising:
    receiving a first set of medical imaging data representing hard tissue facial anatomy of a patient and a scan prosthesis while the patient is wearing the scan prosthesis against soft tissue;
    receiving a second set of medical imaging data representing the scan prosthesis;
    processing the second set of medical imaging data to create a virtual three-dimensional model of the scan prosthesis;
    processing the first and second sets of medical imaging data to create a virtual three-dimensional model of the hard tissue facial anatomy;
    creating a modified hard tissue model by adding support structures to the virtual three-dimensional model of the hard tissue facial anatomy such that placing the virtual three-dimensional model of the scan prosthesis against the support structures results in a space between the modified hard tissue model and the virtual three-dimensional model of the scan prosthesis that is representative of the soft tissue; and
    forming a solid modified hard tissue model by forming the modified hard tissue model in a solid material.

13. The method of claim 12, further comprising:
    forming a solid representation of the virtual three-dimensional model of the scan prosthesis;
    applying a moldable material between the solid modified hard tissue model and the solid representation of the virtual three-dimensional model of the scan prosthesis; and
    pressing the solid representation of the virtual three-dimensional model of the scan prosthesis onto the solid modified hard tissue model to form the moldable material into a shape of the soft tissue.

14. The method of claim 13, wherein forming the solid representation of the virtual three-dimensional model of the scan prosthesis comprises forming the solid representation of the virtual three-dimensional model of the scan prosthesis with a solid freeform fabrication process.

15. The method of claim 12, further comprising:
    applying a moldable material between the solid modified hard tissue model and the scan prosthesis; and pressing the scan prosthesis onto the solid modified hard tissue model to form the moldable material into a shape of the soft tissue.

16. The method of claim 12, wherein the scan prosthesis includes a fiducial marker, and wherein processing the first and second sets of medical imaging data to create the virtual three-dimensional model of the hard tissue facial anatomy comprises:
aligning the first set of medical imaging data with the second set of medical imaging data using the fiducial marker; and
subtracting the second set of medical imaging data from the first set of medical imaging data.

17. The method of claim 16, wherein the fiducial marker is a radiographic marker.

18. The method of claim 12, wherein the scan prosthesis is a denture.

19. The method of claim 12, wherein forming the solid modified hard tissue model comprises forming the modified hard tissue model with a solid freeform fabrication process.

20. The method of claim 12, wherein the first set of medical imaging data comprises computed tomography scan data.

* * * * *